(12) United States Patent
Gasper

(10) Patent No.: US 8,293,172 B2
(45) Date of Patent: Oct. 23, 2012

(54) METHOD OF DISPENSING A VOLATILE MATERIAL

(75) Inventor: Thomas P. Gasper, Germantown, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 412 days.

(21) Appl. No.: 12/565,530

(22) Filed: Sep. 23, 2009

(65) Prior Publication Data
US 2010/0078497 A1 Apr. 1, 2010

Related U.S. Application Data

(60) Provisional application No. 61/194,584, filed on Sep. 29, 2008, provisional application No. 61/194,622, filed on Sep. 29, 2008.

(51) Int. Cl.
 A61L 9/00 (2006.01)
 G01D 11/26 (2006.01)
 A62B 7/08 (2006.01)
 F24H 7/00 (2006.01)
 H05B 6/10 (2006.01)
 B05B 1/08 (2006.01)
(52) U.S. Cl. ............... 422/5; 422/1; 422/3; 422/105; 422/119; 422/125; 392/340; 219/635; 219/666; 219/50; 239/99
(58) Field of Classification Search ............ 422/1, 3, 422/5, 105, 119, 125, 306; 392/340; 219/635, 219/666, 50; 239/99
 See application file for complete search history.

(56) References Cited

U.S. PATENT DOCUMENTS

| 3,410,488 A | 11/1968 | Sugimura |
| 3,948,445 A | 4/1976 | Andeweg |
| 4,425,302 A | 1/1984 | Pons Pons |
| 4,603,030 A | 7/1986 | McCarthy |
| 4,849,606 A | 7/1989 | Martens, III et al. |
| 4,924,068 A | 5/1990 | Henri |

(Continued)

FOREIGN PATENT DOCUMENTS

EP 1214949 A2 6/2002

(Continued)

OTHER PUBLICATIONS

PCT/US2009/005365 International Search Report and Written Opinion Dated Nov. 26, 2009.

*Primary Examiner* — Jill Warden
*Assistant Examiner* — Monzer Chorbaji

(57) ABSTRACT

A method of dispensing a volatile material includes the steps of providing power to a volatile material diffuser having a diffusion element and operating the diffusion element for a first period of time, wherein the diffusion element is continuously activated and deactivated during the period of time at a first duty cycle having a first on time and a first off time. Still further, the method includes the step of operating the diffusion element for a final period of time, wherein the diffusion element is continuously activated and deactivated during the final period of time at a final duty cycle having a final on time and a final off time. The first duty cycle is less than about 100% such that the first off time is greater than about 0 seconds and the final duty cycle is about 100% such that the final off time is about 0 seconds and wherein the final period of time begins after the first period of time has finished.

17 Claims, 10 Drawing Sheets

U.S. PATENT DOCUMENTS

| | | | |
|---|---|---|---|
| 5,029,729 A | 7/1991 | Madsen et al. | |
| 5,111,477 A | 5/1992 | Muderlak et al. | |
| 5,175,791 A | 12/1992 | Muderlak et al. | |
| 5,297,988 A | 3/1994 | Nishino et al. | |
| 5,429,180 A * | 7/1995 | Nishino et al. | 165/41 |
| 5,591,395 A | 1/1997 | Schroeder et al. | |
| 5,591,409 A | 1/1997 | Watkins | |
| 5,647,053 A | 7/1997 | Schroeder et al. | |
| 5,937,140 A | 8/1999 | Leonard et al. | |
| 6,204,623 B1 | 3/2001 | Levy et al. | |
| 6,390,453 B1 | 5/2002 | Frederickson et al. | |
| 6,478,440 B1 | 11/2002 | Jaworski et al. | |
| 6,581,915 B2 | 6/2003 | Bartsch et al. | |
| 6,603,924 B2 | 8/2003 | Brown et al. | |
| 6,661,967 B2 | 12/2003 | Levine et al. | |
| 6,712,287 B1 | 3/2004 | Le Pesant et al. | |
| 6,790,408 B2 | 9/2004 | Whitby et al. | |
| 6,792,199 B2 | 9/2004 | Levine et al. | |
| 6,854,717 B2 | 2/2005 | Millan | |
| 6,857,580 B2 | 2/2005 | Walter et al. | |
| 6,862,403 B2 | 3/2005 | Pedrotti et al. | |
| 6,917,754 B2 | 7/2005 | Pedrotti et al. | |
| 6,920,282 B2 | 7/2005 | He et al. | |
| 6,923,383 B1 | 8/2005 | Joshi et al. | |
| 6,931,202 B2 | 8/2005 | Pedrotti et al. | |
| 6,996,335 B2 | 2/2006 | Zobele | |
| 7,036,800 B2 | 5/2006 | Ellis | |
| 7,223,361 B2 | 5/2007 | Kvietok et al. | |
| 7,249,719 B2 | 7/2007 | He et al. | |
| 7,484,716 B2 | 2/2009 | Morie et al. | |
| 7,493,028 B2 | 2/2009 | DeWitt et al. | |
| 2004/0101447 A1 | 5/2004 | Tajima et al. | |
| 2006/0193611 A1 | 8/2006 | Ruiz Ballesteros et al. | |
| 2007/0012718 A1 | 1/2007 | Schramm et al. | |
| 2007/0160492 A1* | 7/2007 | Spector | 422/5 |
| 2007/0166185 A1 | 7/2007 | Bartels | |
| 2007/0166186 A1 | 7/2007 | Stec | |
| 2007/0280653 A1 | 12/2007 | Viera | |
| 2008/0014125 A1 | 1/2008 | He et al. | |
| 2008/0095522 A1 | 4/2008 | Deflorian et al. | |
| 2008/0191370 A1 | 8/2008 | Pankhurst et al. | |

FOREIGN PATENT DOCUMENTS

| | | |
|---|---|---|
| EP | 1407790 A1 | 4/2004 |
| GB | 2443925 A | 5/2008 |
| JP | 5173648 | 7/1993 |
| WO | WO2007064189 | 6/2007 |
| WO | WO2007079046 | 7/2007 |
| WO | WO2008149065 | 12/2008 |

* cited by examiner

METHOD OF DISPENSING A VOLATILE MATERIAL

CROSS REFERENCE TO RELATED APPLICATIONS

This application claims the benefit of U.S. Provisional Application No. 61/194,584, filed Sep. 29, 2008, and U.S. Provisional Application No. 61/194,622, filed Sep. 29, 2008. Each of the aforementioned applications is incorporated herein by reference in its entirety.

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention relates to methods of dispensing volatile materials, and more particularly, to methods of dispensing volatile material according to pre-established programming that aids in diminishing or preventing habituation.

2. Description of the Background

A multitude of volatile material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing volatile materials from volatile material diffusers are also known in the art. For example, some diffusers include a heating element for heating a volatile material to promote vaporization thereof. Other diffusers employ a fan or blower to generate air flow to direct volatile material out of the diffuser into the surrounding environment. In another type of diffuser, one or more volatile materials may be emitted from the diffuser using a bolus generator that delivers a pulse of air to eject a scent ring. Still other diffusers that dispense volatile materials utilize ultrasonic means to dispense the volatile materials therefrom. In addition, other diffusers utilize more than one of these means to vaporize and/or disperse volatile materials.

A problem with past volatile material diffusers is that a user may become accustomed to or habituated to a particular volatile material. Habituation is a phenomenon that occurs when a person becomes use to a particular volatile material or fragrance such that they no longer perceive the volatile material. Various diffusers have attempted to alleviate this problem. Some diffusers include a switch or other mechanism that is controlled by the user, whereby the user can change the intensity level at which the volatile material is dispensed. The manner in which the intensity level of the volatile material is varied is either mechanical or electrical in nature.

Other diffusers include one or more containers having a volatile material therein, wherein a fan and/or a heater is periodically actuated to dispense the volatile material at particular time intervals.

Still other diffusers include at least two fragrances that are emitted in an alternating sequence. One such diffuser includes a housing having first and second heaters, wherein the housing is adapted to releasably secure first and second containers having first and second wicks respectively extending therefrom. The wicks are disposed adjacent the heaters and the heaters are turned on and off in an alternating sequence to alternately emit the first and second fragrances.

SUMMARY OF THE INVENTION

According to one aspect of the present invention, a method of dispensing a volatile material includes the step of providing power to a volatile material diffuser having a diffusion element. The method further includes the step of operating the diffusion element for a first period of time, wherein the diffusion element is continuously activated and deactivated during the period of time at a first duty cycle having a first on time and a first off time. Still further, the method includes the step of operating the diffusion element for a final period of time, wherein the diffusion element is continuously activated and deactivated during the final period of time at a final duty cycle having a final on time and a final off time. The first duty cycle is less than about 100% such that the first off time is greater than about 0 seconds and the final duty cycle is about 100% such that the final off time is about 0 seconds and wherein the final period of time begins after the first period of time has finished.

According to a further aspect of the present invention, a method of dispensing a volatile material includes the step of providing power to a volatile material diffuser having a diffusion element. The method further includes the step of operating the diffusion element for a first period of time, wherein the diffusion element is continuously activated and deactivated during the first period of time at a first duty cycle. Still further, the method includes the steps of interrupting operation of the diffusion element during the first period of time to operate the diffusion element at a second duty cycle for an interrupt period of time. The first and second duty cycles are different.

According to yet another aspect of the present invention, a method of dispensing a volatile material includes the step of providing power to a volatile material diffuser having a diffusion element. The method further includes the step of operating the diffusion element for a first period of time, wherein the diffusion element is continuously activated and deactivated during the first period of time at a first duty cycle. Still further, the method includes the step of operating the diffusion element for a second period of time following the first period of time, wherein the diffusion element is continuously activated and deactivated during the second period of time at a second duty. The method still further includes the step of interrupting operation of the diffusion element during at least one of the first and second periods of time to operate the diffusion element at a third duty cycle for an interrupt period of time.

Other aspects and advantages of the present invention will become apparent upon consideration of the following detailed description and the attached drawings, in which like elements are assigned like reference numerals.

DETAILED DESCRIPTION

Figure 1:
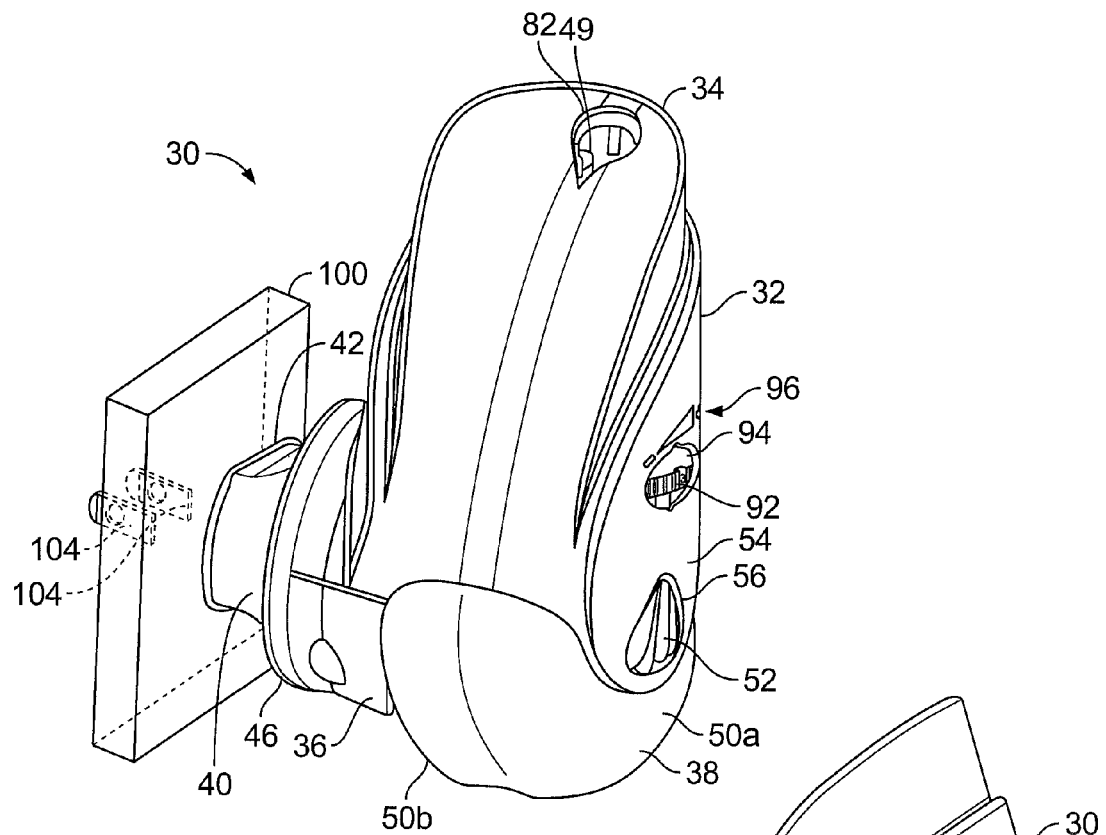
FIG. 1 is a perspective view of a volatile material diffuser according to the present invention.
Figure 2:
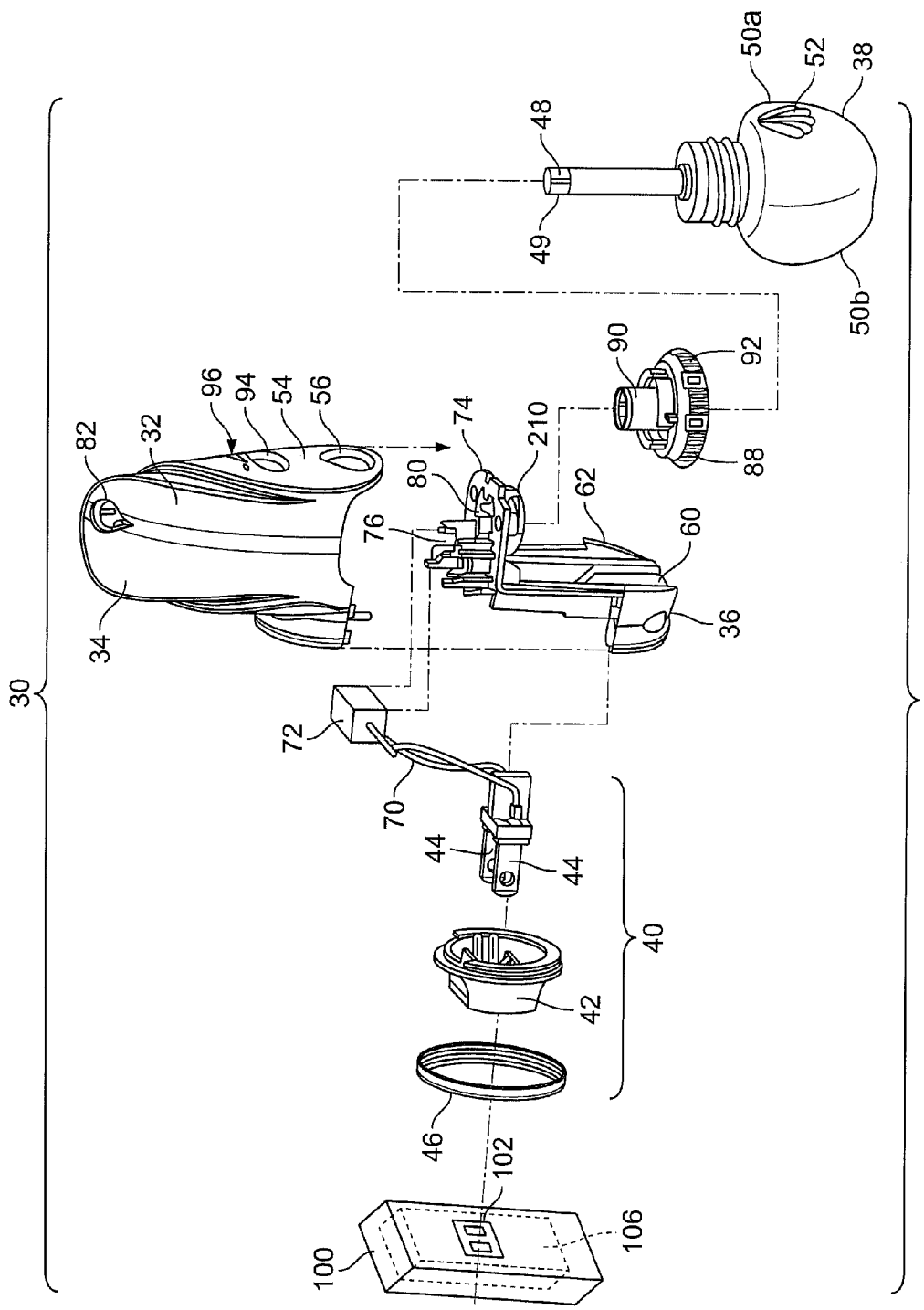
FIG. 2 is an exploded view of the volatile material diffuser of FIG. 1.

Referring to FIGS. 1 and 2, a volatile material diffuser 30 generally includes a multi-piece housing 32 having an upper housing portion 34 and a lower housing portion 36 fastened together by heat-staking or other suitable fastening means, including, for example, rivets, press fit, snap fit, screws, ultrasonic welding, adhesives, and the like. A container 38 is detachably retained within the lower housing portion 36. The diffuser 30 further includes an electrical plug assembly 40 having a plug portion 42 rotatably secured between the upper and lower housing portions 34, 36 and electrical contacts 44 extending outwardly from the plug portion 42 for insertion into a conventional wall outlet (not shown) or other electronic device, as discussed in greater detail hereinafter. A collar 46 is disposed over the plug portion 42 to ensure proper engagement of the upper and lower housing portions 34, 36 around the plug portion 42.

Figure 3:
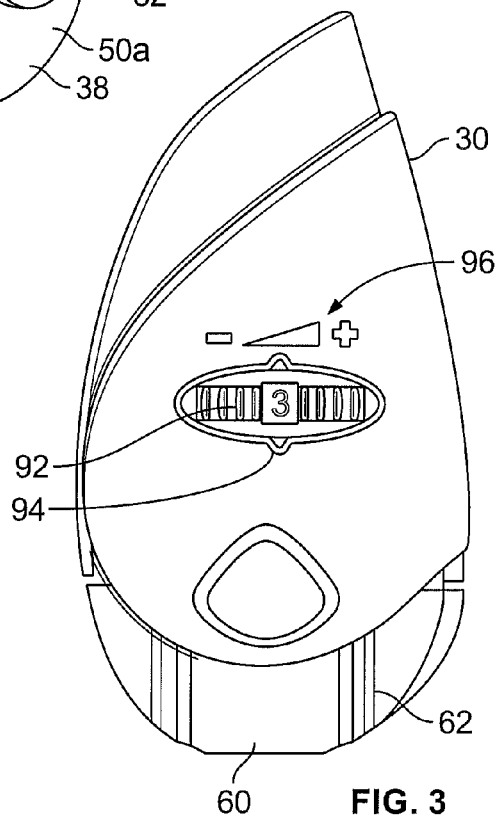
FIG. 3 is a front elevational view of the volatile material diffuser of FIG. 1.

The container 38 includes a volatile material disposed therein and a wick 48 in contact with the volatile material and extending out of the container 38. The wick 48 is adapted to draw the volatile material in the form of a liquid out of the container 38 toward an upper portion 49 of the wick 48. The container 38 is adapted for insertion into and securement within the housing 32. In particular, front and rear surfaces 50a, 50b of the container 38 include shell-shaped protrusions 52 (only the shell-shaped protrusion on the front surface 50a is shown) extending therefrom. The container 38 is inserted into the lower housing portion 36 by inserting the wick 48 into the housing 32 and thereafter moving the container 38 upwardly. As the container 38 is moved upwardly, the shell-shaped protrusion 52 on the front surface 50a of the container 38 causes a slight outward deformation of a front wall 54 of the upper housing portion 34 to allow the protrusion 52 to pass into a similarly-shaped aperture 56 in the front wall 54 of the upper housing portion 34. As the container 38 is moved upwardly, the shell-shaped protrusion (not shown) on the rear surface 50b of the container 38 moves along a groove 60 formed in a front surface 62 of the lower housing portion 36, as seen in FIGS. 2 and 3. As the shell-shaped protrusion 52 on the front surface 50a of the container 38 snaps into the aperture 56, a top portion of the shell-shaped protrusion (not shown) on the rear surface 50b of the container 38 comes to rest at a top portion of the groove 60 that has a shape similar to a top portion of the shell-shaped protrusion. Pulling the container 38 in a downward direction causes a slight outward deformation of the front wall 54 of the upper housing portion 34 to allow a user to remove and replace the container 38.

Although the container 38 is shown as being secured within the housing 32 by shell-shaped protrusions 52, a neck portion of the container 38 may alternatively be designed to snap or screw into the housing 32.

The volatile material within the container 38 may be any type of volatile material, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof.

Referring to FIG. 2, the electrical contacts 44 are electrically connected via conventional electrical conductors 70, such as wires or electrodes, to a heating device 72. The lower housing portion 36 includes a horizontal platform 74 extending generally perpendicularly from the front surface 62 of the lower housing portion 36. A heating device support 76 extends upwardly from the platform 74 for holding the heating device 72. When the container 38 is inserted into the diffuser 30, the wick 48 thereof extends through a channel 80 in the platform 74 such that the top portion 49 of the wick 48 is disposed adjacent the heating device 72. The heating device 72 applies heat to the wick 48 to enhance the rate at which the volatile material therein is evaporated. As volatile material is evaporated from the wick 48, the volatile material moves upwardly and out an aperture 82 disposed in the upper housing portion 34.

The diffuser 30 further includes an adjustment mechanism 88 that positions an upper portion of the wick 48 in one of a number of discrete positions relative to the heating device 72 to change the intensity at which the volatile material is evaporated. The adjustment mechanism 88 includes a hollow cylindrical portion 90 that surrounds and engages the upper portion of the wick 48 to move same toward and away from the heating device 72. The adjustment mechanism 88 is similar to the adjustment mechanism described in Pedrotti et al. U.S. Pat. No. 6,931,202, the disclosure of which is hereby incorporated by reference in its entirety. A dial portion 92 is provided for rotating the cylindrical portion 90 to change the intensity at which the volatile material is evaporated. The dial portion 92 extends through an opening 94 in the front wall 54 of the upper housing portion 34 such that a user can rotate the dial portion 92. An indicator 96 is preferably disposed on the front wall 54 of the upper housing portion 34 to provide an indication to a user of how to rotate the dial portion 92 to increase and decrease an intensity at which the volatile material is evaporated.

The diffuser 30 described with respect to FIGS. 1-3 is described in greater detail in Zobele U.S. Pat. No. 6,996,335, the disclosure of which is incorporated herein in its entirety.

Referring again to FIGS. 1 and 2, the diffuser 30 includes an adapter box 100 having a conventional electrical socket 102 therein (FIG. 2), wherein the electrical contacts 44 extending from the plug portion 42 of the diffuser 30 are inserted into and retained within the electrical socket 102. The adapter box 100 includes a set of electrical contacts 104 extending therefrom for insertion into a conventional wall socket (not shown) to power the diffuser 30. The adapter box 100 includes a printed circuit board (PCB) 106 (FIG. 2) disposed therein for controlling the functionality of the heating device 72, as discussed in greater detail hereinafter. The adapter box 100 may be used with any diffuser known in the art. Optionally, the adapter box 100 may be replaced by a PCB 106 that implements the same or similar functionality and which is disposed within the diffuser 30.

Figure 4:
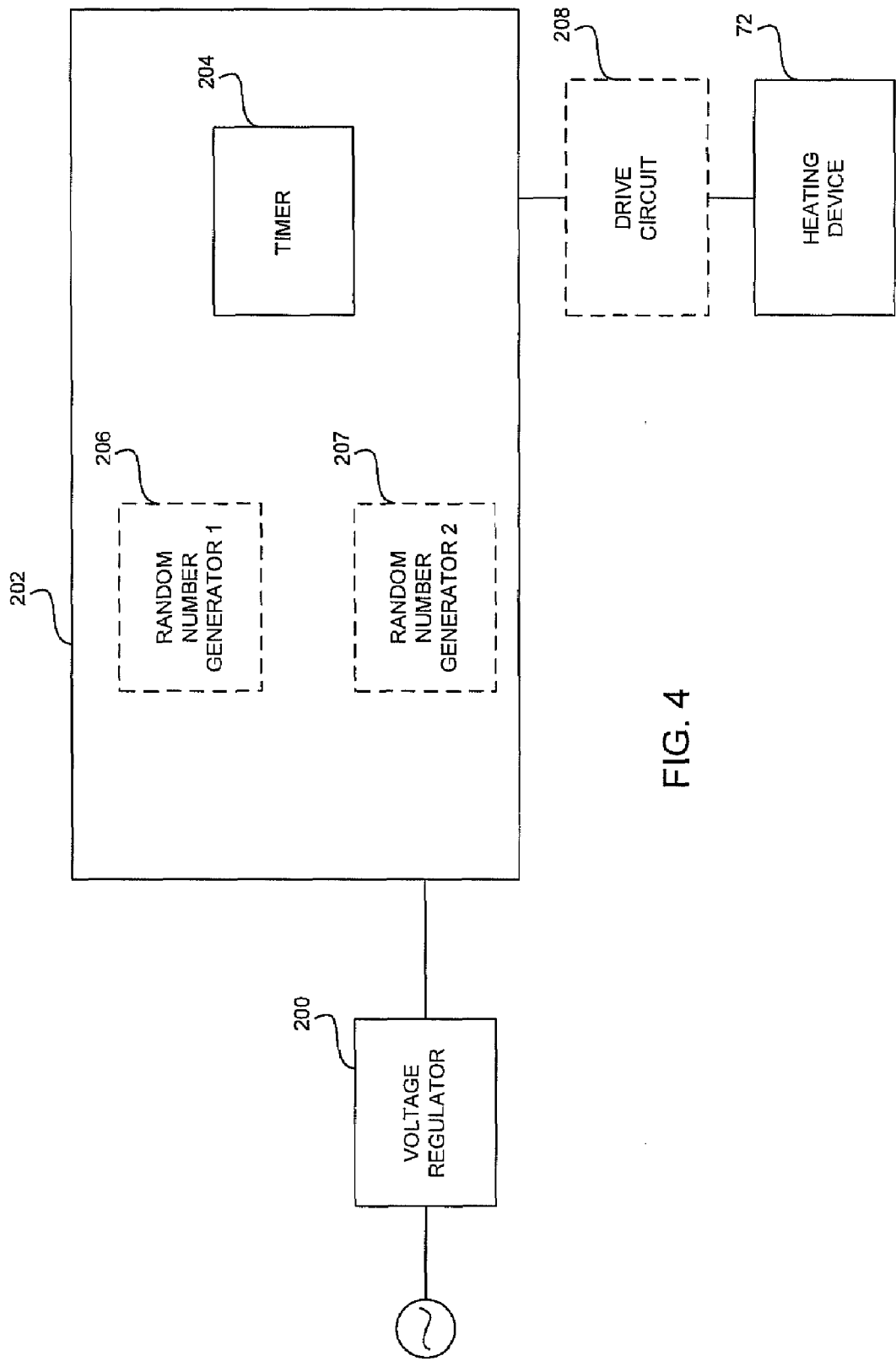
FIG. 4 is a block diagram of circuits including a programmable device for controlling application of power to a heating device of the diffuser of FIGS. 1-3.

FIG. 4 depicts a block diagram of circuits for controlling the operation of the heating device 72 of the volatile material diffuser 30. The circuits of FIG. 4 are carried by, for example, the PCB 106. A voltage regulator 200 known to those of ordinary skill in the art provides a regulated voltage Vcc to a programmable device 202. In one embodiment, the programmable device 202 is an 8-pin flash based 8-bit CMOS microcontroller PIC12F629 sold by Microchip Technology Inc. of Chandler, Ariz. The programmable device 202 includes a timer 204 and/or a random number generator 206. An optional drive circuit 208 is connected between the programmable device 202 and the heating device 72. The optional drive circuit 208 may be carried by the PCB 106 and is utilized if the programmable device 202 cannot develop suitable power to operate the heating device 72.

Figure 4A:
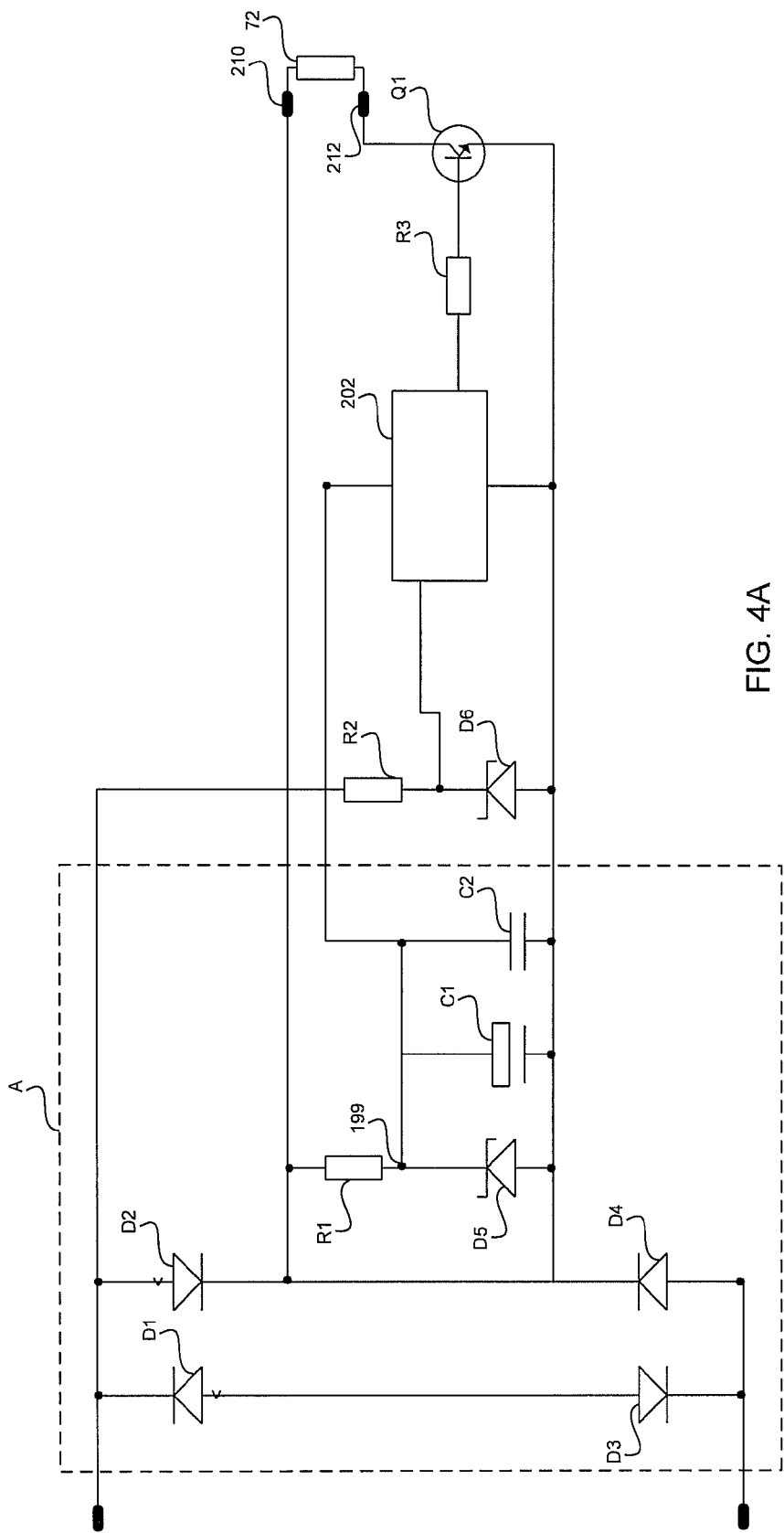
FIG. 4A is a schematic of one embodiment of the circuits of FIG. 4.

FIG. 4A illustrates one embodiment of the circuits of FIG. 4, wherein the voltage regulator 200 is shown in a block A. The block A includes four diodes D1-D4 coupled in a full bridge configuration to develop a full wave rectified voltage from a 120 VAC power supply. A resistor R1 and a zener diode D5 are connected in parallel across the full wave rectified voltage and first and second capacitors C1 and C2 are connected in parallel between a terminal 199 and ground for filtering purposes. The components R1, D5, C1, and C2 together develop a 5V voltage for the programmable device 202. A zero-crossing of the A.C. voltage input is sensed by circuitry comprising a resistor R2 and a zener diode D6 to provide a timing reference to the programmable device 202. An output of the programmable device provides a control signal via a resistor R3 to a base of a transistor Q1. The collector of the transistor Q1 is connected to a first terminal 210 of the heating device 72 and an emitter of the transistor Q1 is connected to ground. A second terminal 212 of the heating device 72 is connected to the full wave rectified voltage. The programmable device 202 controls how much of each pulse of the full wave rectified voltage that is applied to the heating device 72 by turning the transistor Q1 on and off for a predetermined amount of time during each pulse of the full wave rectified voltage. While this is not a conventional implementation of pulse width modulation (PWM), the conduction time of the heating device 72 is varied as if a PWM signal were applied thereto.

In operation, the programmable device 202 senses the zero crossing of the A.C. power supply once every 8 milliseconds. The programmable device 202 is programmed to save parameters, such as how much time has elapsed since the timer 204 was activated, when the programmable device 202 determines that the diffuser 30 has been disconnected form the A.C. power supply. Specifically, when the diffuser 30 is disconnected from the A.C. power supply, the programmable device 202 saves current parameters because the programmable device 202 does not sense the zero-crossing for a period of more than 8 milliseconds while the capacitors C1 and C2 discharge. The programmable device 202 subsequently restores the saved parameters when power is reapplied to the diffuser 30 and the programmable device 202 senses the zero crossing.

Figure 5A:
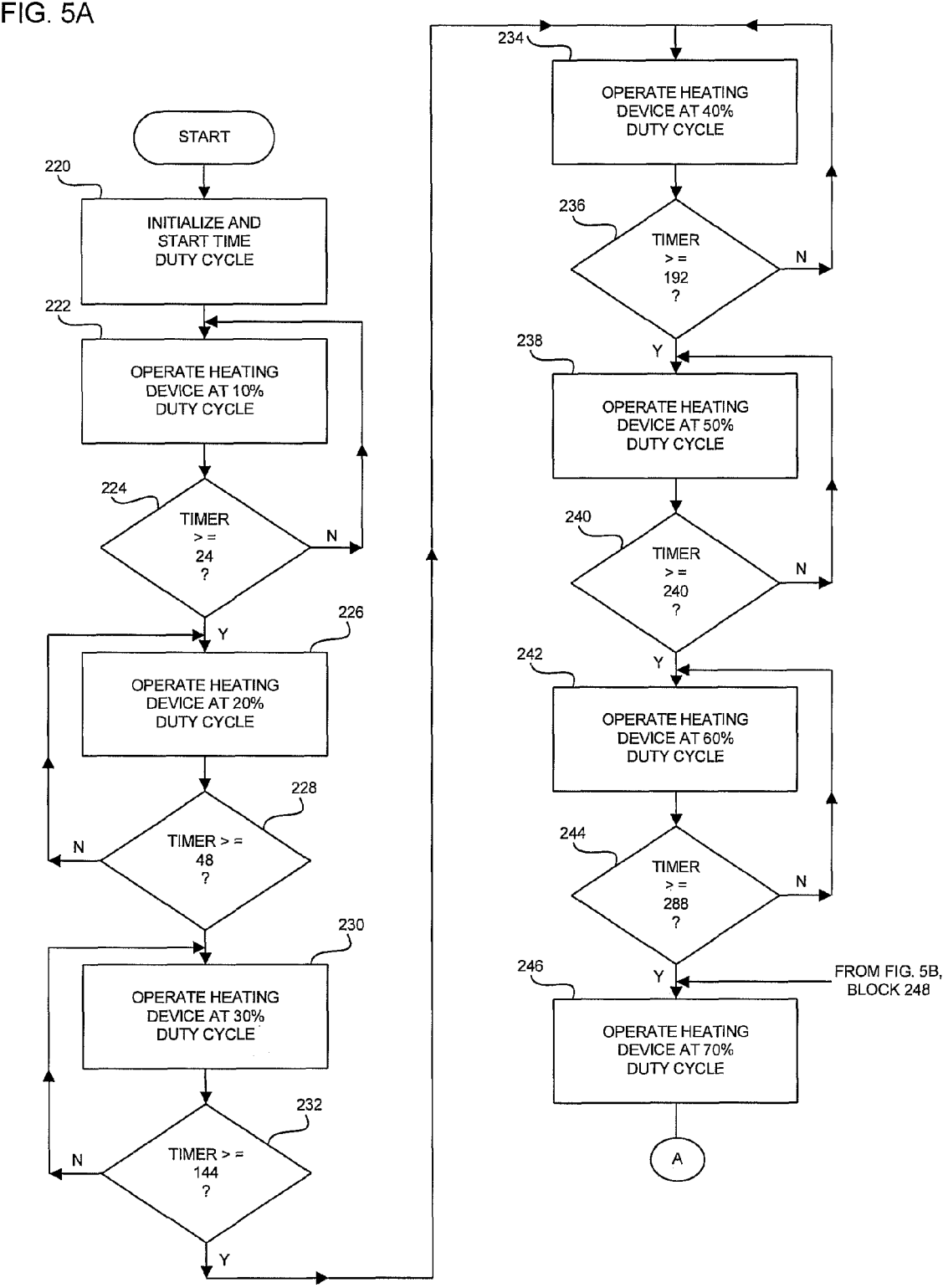
FIGS. 5A and 5B depict a flow chart illustrating a first embodiment of programming that may be implemented by a programmable device for operation of the heating device of the diffuser of FIGS. 1-3.
Figure 5B:
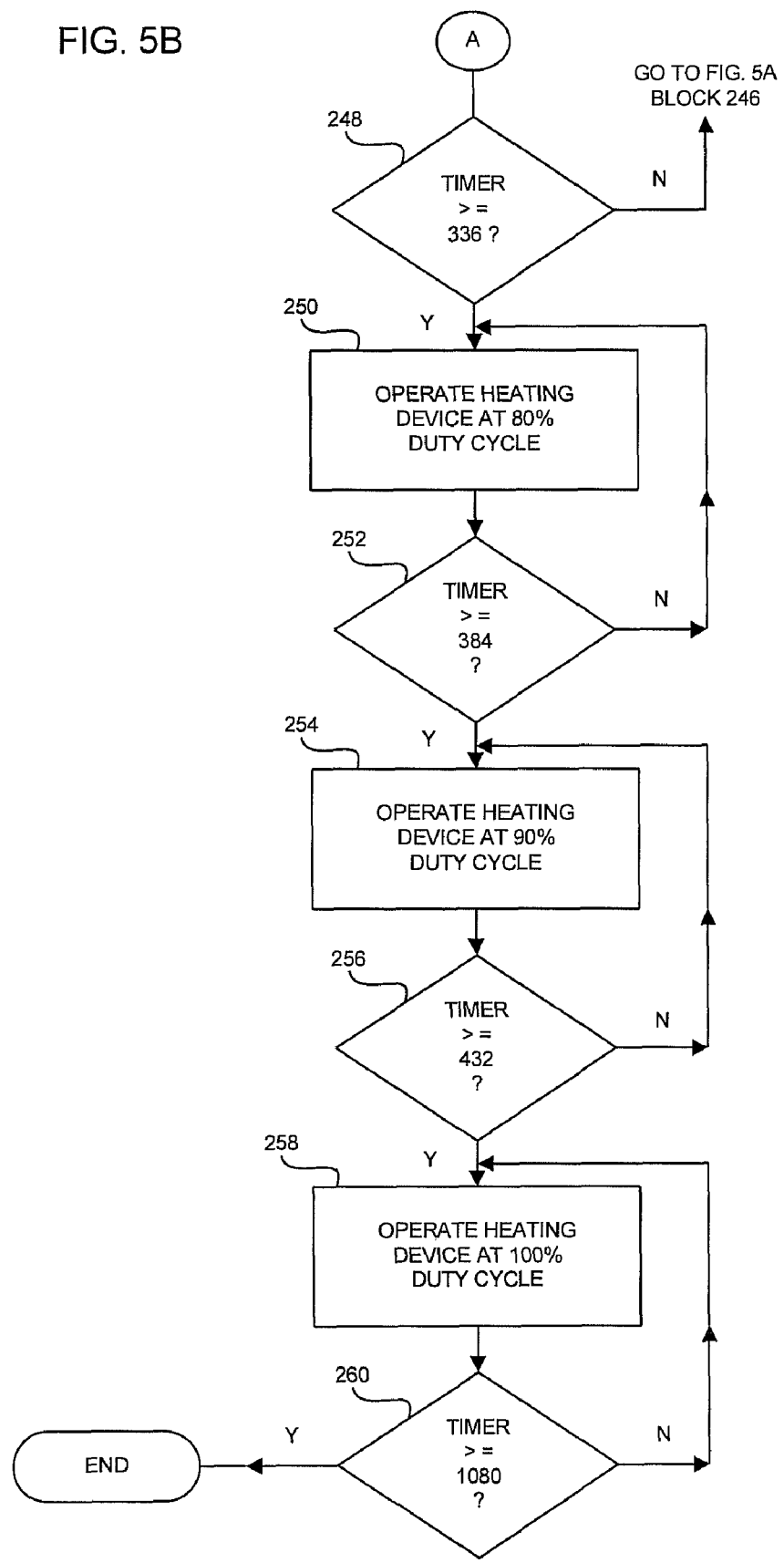

FIG. 5A illustrates a first embodiment of programming that may be implemented by the programmable device 202 to operate the heating device 72, for example, or any other diffusion element known in the art. In the embodiment of FIGS. 5A and 5B, the timer 204 but no random number generator 206 is utilized. Operation begins at a block 220 after the adapter box 100 or diffuser 30 is plugged into an electrical outlet, wherein the block 220 initializes and starts the timer 204. Next, control passes to a block 222 that operates the heating device at a 10% duty cycle, wherein the duty cycle is defined by an on or active time of the diffusion element divided by the total period, which includes the on and an off time. During operation, the heating device or other diffusion element is continuously activated and deactivated according to the set duty cycle. Following the block 222, control passes to a block 224 that determines whether a period of 24 hours has elapsed since the block 220 activated the timer 204. If not, control returns to block 222. If a period of 24 hours has elapsed, control passes to a block 226 that operates the heating device at a 20% duty cycle. The block 226 passes control to a block 228 that determines whether a period of 48 hours has passed since the block 220 started the timer 204. Control returns to the block 226 if the period since the timer 204 started is less than 48 hours. Otherwise, control passes to a block 230 that operates the heating device 72 at a 30% duty cycle. Following the block 230, a block 232 determines whether a period of 144 hours has elapsed since the block 220 initialized the timer 204. In the event that a period of less than 144 hours has elapsed since the timer 204 was initiated, control returns to the block 230. Otherwise, if a period of 144 hours or more has elapsed, control passes to a block 234 that operates the heating device at a 40% duty cycle. The block 234 passes control to a block 236 that determines whether a period of 192 hours has elapsed since the timer 204 started. If not, control returns to the block 234. If a period of 192 hours has elapsed, control passes to a block 238 that operates the heating device 72 at a 50% duty cycle. The block 238 thereafter passes control to a block 240 that determines whether a period of 240 hours has elapsed since the timer 204 was initiated at the block 220. If a period of less than 240 hours has elapsed since the timer 204 was started, control returns to the block 238. Otherwise, if a period of 240 hours or more has elapsed, control passes to a block 242 that operates the heating device 72 at a 60% duty cycle. Following the block 242, a block 244 determines whether it has been at least 288 hours since the block 220 activated the timer 204. If not, control returns to the block 242. If a period of at least 288 hours has elapsed since the timer 204 started, control passes to a block 246 that operates the heating device 72 at a 70% duty cycle.

Referring to FIG. 5B, control passes from the block 246 to a block 248 that determines whether a period of 336 hours has elapsed since the block 220 activated the timer 204. If not, control returns to the block 246. Otherwise, if a period of at least 336 hours has elapsed, control passes to a block 250 that activates the heating device 72 at a 80% duty cycle. Following the block 250, control passes to a block 252 that determines whether 384 hours has passed since the block 220 started the timer 204. If less than 384 hours has elapsed since the timer 204 started, control returns to the block 250. If a period of at least 384 hours has elapsed, control passes to a block 254 that operates the heating device at a 90% duty cycle and thereafter passes control to a block 256 that determines whether a period of 432 hours has elapsed. If not, control returns to block 254. Control passes to a block 258 if the block 256 determines that a period of 432 hours has passed since the timer 204 started and the block 258 operates the heating device 72 at a 100% duty cycle. Thereafter, control passes to a block 260 that determines whether a period of 1080 hours has elapsed since the timer 204 was initiated. Control returns to the block 258 unless the block 260 determines that the timer 204 has operated for 1080 hours.

Figure 6:
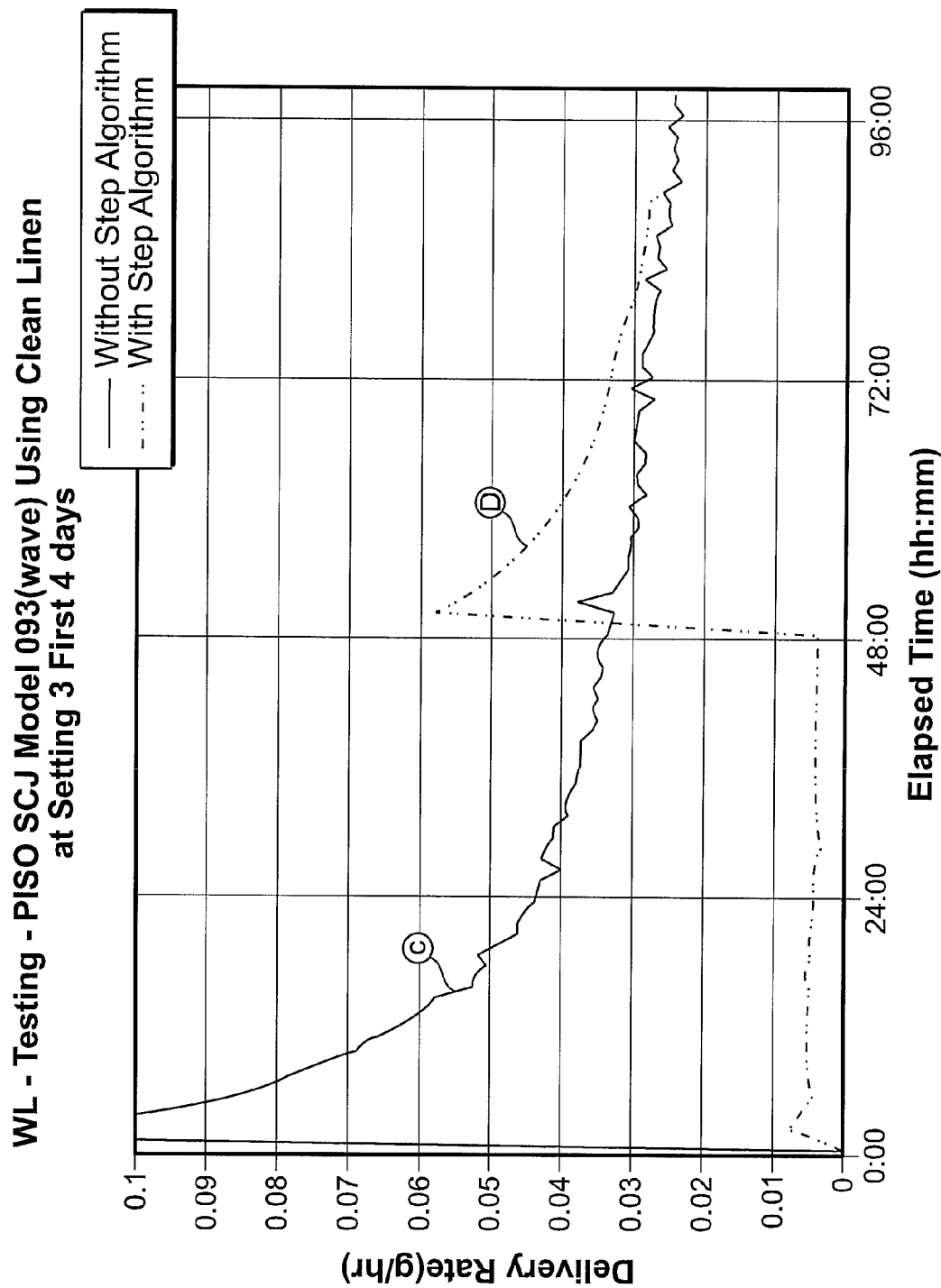
FIG. 6 is a plot depicting delivery rate versus time for a sample testing cycle of the programming depicted in FIG. 5.

With reference to FIG. 6, a sample plot of the delivery rate (grams/hour) versus time (hours) illustrates an advantage that is derived from using the programming of FIG. 5 to control the heating device 72. A solid line C represents a delivery rate of the heating device 72 when the heating device 72 is operated at a duty cycle of 100% over a testing period of 96 hours. The delivery rate shown by the solid line C steadily decreases over time and would continue to do so if operated past 96 hours. In contrast, broken line D illustrates the delivery rate of the heating device 72 when the duty cycle of the heating device 72 is varied over time according to the programming of FIG. 5. Unlike the delivery rate shown by the solid line C, the delivery rate shown by the broken line D indicates a spike in the delivery rate when the duty cycle of the heating device is increased from 10% to 20% after 48 hours of operation according to the programming of FIG. 5. It is believed that similar spikes would occur after each increase in duty cycle, thereby providing bursts of volatile material that work to reduce, minimize, or prevent habituation to the volatile material.

Figure 7:
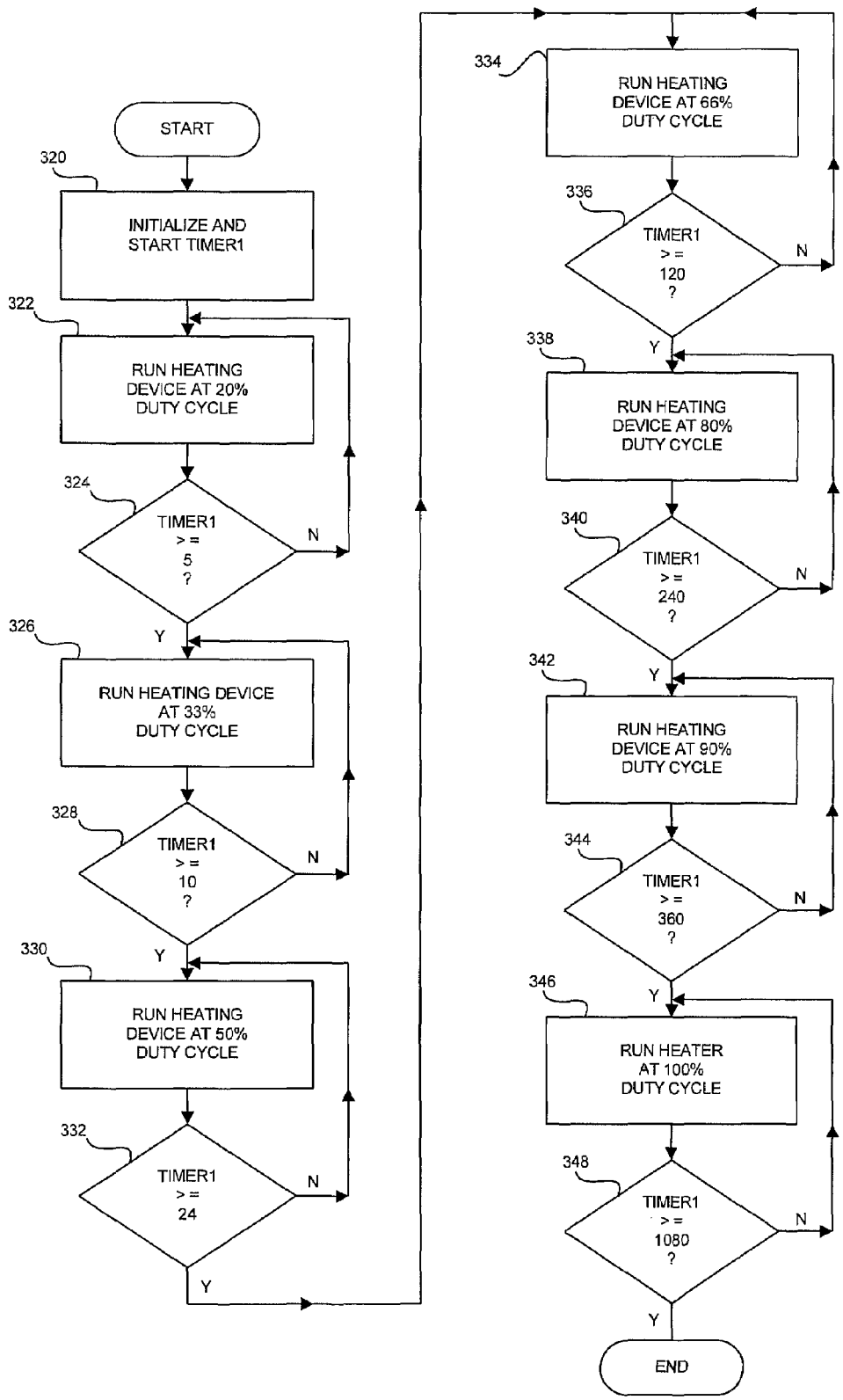
FIG. 7 depicts a flow chart illustrating a second embodiment of programming that may be implemented by a programmable device for operation of the heating device of the diffuser of FIGS. 1-3.

FIG. 7 illustrates a second embodiment of programming that may be implemented by the programmable device 302 to operate the heating device 72, for example, or any other diffusion element known in the art. In the embodiment of FIG. 7, the timer 204 but no random number generator 206 is utilized. Operation begins at a block 320 after the adapter box 100 or diffuser 30 is plugged into an electrical outlet, wherein the block 320 initializes and starts the timer 204. Next, control passes to a block 322 that operates the heating device 72 at a 20% duty cycle. Following the block 322, control passes to a block 324 that determines whether a period of 5 hours has elapsed since the block 320 activated the timer 204. If not, control returns to the block 322. If a period of 5 hours has elapsed, control passes to a block 326 that operates the heating device 72 at a 33% duty cycle and passes control to a block 328. The block 328 determines whether a period of 10 hours has elapsed since the block 320 activated the timer 204. If not, control returns to the block 326. When the block 328 determines that a period of 10 hours has elapsed, control passes to a block 330. The block 330 operates the heating device 72 at a duty cycle of 50% and passes control to a block 332 that checks whether a period of 24 hours has elapsed since the block 320 started the timer 204. If a period of less than 24 hours has elapsed, control returns to the block 330. If a period of 24 hours has elapsed since the timer 204 was initiated, control passes to a block 334 that activates the heating device 72 at a 66% duty cycle. Following the block 334, control passes to a block 336 that determines whether a period of 120 hours has elapsed since the block 320 initiated the timer 204. If not, control returns to the block 334. If a period of 120 hours has elapsed, control passes to a block 338 that operates the heating device at 80% duty cycle. The block 338 thereafter passes control to a block 340 that determines whether a period of 240 hours has elapsed since the timer 204 was initiated. The block 340 returns control to the block 338 if the block 340 determines that a period of less than 240 hours has elapsed. Otherwise, the block 340 passes control to a block 342 that operates the heating device 72 at 90% duty cycle and thereafter passes control to a block 344. The block 344 determines whether a period of 360 hours has elapsed since the timer 204 was initiated in the block 320. If not, control returns to the block 342. If a period of 360 hours has elapsed, control passes to a block 346 that operates the heating device 72 at a 100% duty cycle. The block 346 passes control to a block 348 that determines whether a period of 1080 hours has elapsed since the timer 204 was started in the block 320. Control returns to the block 346 if a period of less than 1080 hours has elapsed. Otherwise, operation ends at the block 348.

Figure 8:
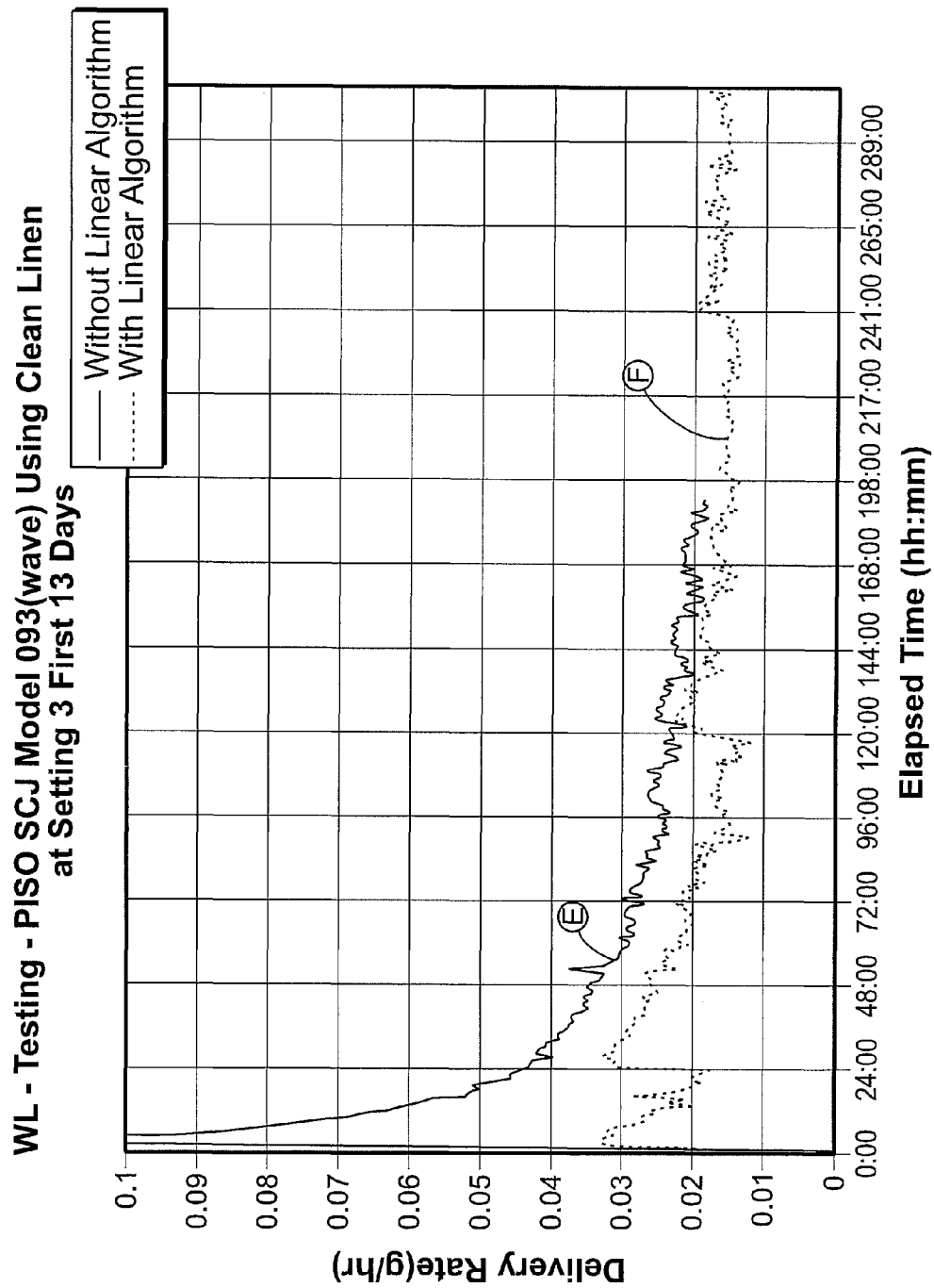
FIG. 8 is a plot depicting delivery rate versus time for a sample testing cycle of the programming depicted in FIG. 7.

With reference to FIG. 8, a sample plot of the delivery rate (grams/hour) versus time (hours) illustrates an advantage that is derived from using the programming of FIG. 7 to control the heating device 72. A solid line E represents a delivery rate of the heating device 72 when the heating device 72 is operated at a duty cycle of 100%. The solid line E ends at 189 hours due to a limited testing period. As shown, the delivery rate shown by the solid line E steadily decreases over time and would continue to do so if the testing period were continued. In contrast, broken line F illustrates the delivery rate of the heating device 72 when the duty cycle of the heating device 72 is varied over time according to the programming of FIG. 7. Unlike the delivery rate shown by the solid line E, the delivery rate shown by the broken line F indicates a steady continuous delivery rate that does not decrease over time.

In a further embodiment of programming, the programming of FIG. 7 may be implemented by the programmable device 202 to operate the heating device 72, for example, or any other diffusion element known in the art, with an interrupt. In particular, at any point during the operation of the programming of FIG. 7, an interrupt may be generated to suspend control from any of the blocks shown in FIG. 7 and cause the random number generator 206 to generate a random number N1. The random number N1 may be any integer and may be selected from any set range of integers that would reduce, minimize, or prevent habituation. Once the random number N1 is generated, the programmable device 202 operates the programming of FIG. 7 until the interrupt gap period of time, which is equal to N1×TIME FACTOR, has elapsed. Once the interrupt gap has elapsed, the programmable device 202 operates the heating device 72 at an interrupt duty cycle for an interrupt period of time. After the interrupt period has elapsed, control may be returned to the last block that was in operation before the interrupt was generated. Thereafter, the interrupt may be generated again (for the same interrupt period or a different interrupt period) after the interrupt gap period of (N1×TIME FACTOR), wherein N1 may be a different integer every time the random number generator 206 is run.

In one embodiment of the programming of FIG. 7, the random number Ni may be the same for a single loop through the programming. In such scenario, the random number N1 may be set at the block 320 and would remain the same for the entire programming and for multiple interrupts. In such example, if, for example, the random number N1=8 were randomly selected, the time factor is 1 hour, and the interrupt period is 1 hour, the programming would implement an interrupt period of 1 hour after an interrupt gap of 8 hours, return to the programming after the 1 hour interrupt period for an interrupt gap of 8 hours, implement another 1 hour interrupt period, and continue this cycle throughout the programming.

In a further embodiment of the programming of FIG. 7, the random number N1 may be different for a single loop through the programming. In such scenario, the random number N1 may be set at the block 320 and would also be set after each interrupt completes. In a specific example, at the block 320, if the random number N1=3 were randomly selected, the time factor is 1 hour, and the interrupt period is 1 hour, the programming would implement an interrupt period of 1 hour after an interrupt gap of 3 hours. After the 1 hour interrupt period, the random number N1 would again be randomly selected, for example, to be N1=9. The programming would then implement an interrupt period of 1 hour (or possibly a different interrupt period) after an interrupt gap of 9 hours. This cycle would continue throughout the programming.

Although an interrupt period of 1 hour is utilized herein, any interrupt period may be utilized that would reduce, minimize, or prevent habituation. In particular, the interrupt period is preferably between 5 minutes and 4 hours, more preferably between about 30 minutes and 2 hours, and most preferably 1 hour. Optionally, although multiple random numbers N1 are selected to create multiple interrupts, a single random number N1 may be selected to create a single interrupt.

Still further, the time factor is preferably between about 10 seconds and about 8 hours, more preferably between about 1 minute and 60 minutes, and most preferably between about 5 minutes and about 30 minutes. The interrupt duty cycle is also preferably, although not necessarily 100%. Optionally, the interrupt duty cycle may be any duty cycle that would create a spike or increase in volatile material emission.

Figure 9:
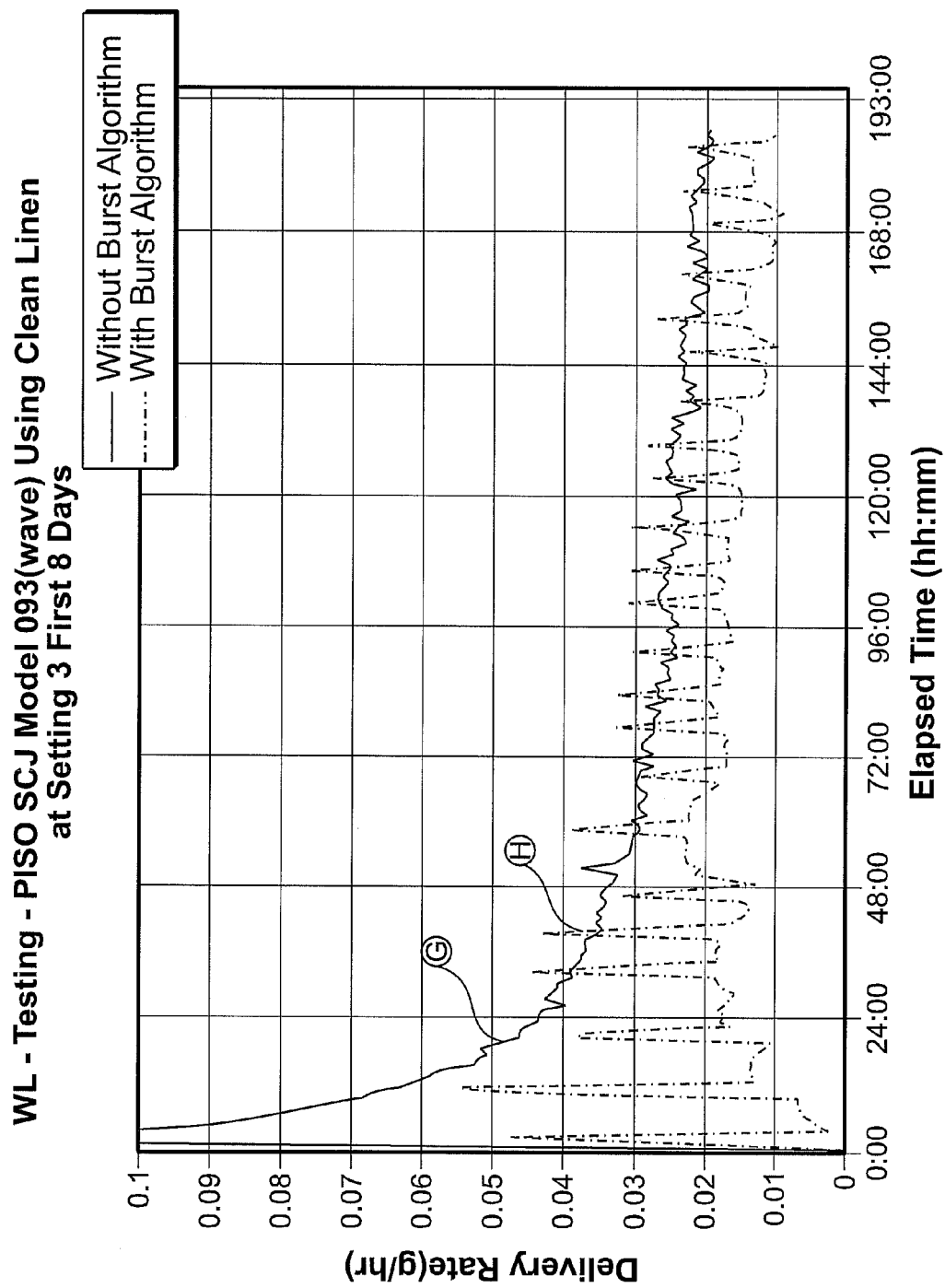
FIG. 9 is a plot depicting delivery rate versus time for a sample testing cycle of the programming depicted in FIG. 7 with an interrupt.

Referring to FIG. 9, a sample plot of the delivery rate (grams/hour) versus time (hours) illustrates an advantage that is derived from using the programming of FIG. 7 with the interrupt, as described above, to control the heating device 72. In particular, in the sample plot of FIG. 9, the random number N1 was randomly selected from the range of integers between and including 6 and 12 with a time factor of 1 hour and an interrupt period of 1 hour. A solid line G represents a delivery rate of the heating device 72 when the heating device 72 is operated at a duty cycle of 100% during the testing period of 193 hours. As shown, the delivery rate shown by the solid line G steadily decreases over time. In contrast, broken line H illustrates the delivery rate of the heating device 72 when the duty cycle of the heating device 72 is varied over time according to the programming of FIG. 7 with the interrupt. Unlike the delivery rate shown by the solid line G, the delivery rate shown by the broken line H indicates a spike in the delivery rate each time the heating device 72 is operated at a 100% duty cycle for a period of an hour according to the interrupt described above with respect to the programming of FIG. 7. This spike in delivery serves to reduce, minimize, or prevent habituation that occurs when a volatile material is dispensed continuously at a single rate of emission.

Although the test sample for the interrupt was conducted using the programming of FIG. 7, the interrupt may be implemented within any programming, for example, that of FIGS. 5A and 5B, programming wherein an active material is emitted at a single constant level, etc.

The duty cycles, time factors, interrupt gaps, and interrupt periods of time associated with each duty cycle, as described in detail with respect to the programming of FIGS. 5A and 5B and FIG. 7 and the interrupt, may be varied, as long as such variations produce results similar to those seen in FIG. 6 and FIGS. 8 and 9 (without or with an interrupt), respectively. In particular, any such variations would still work to reduce, minimize, or prevent habituation in the same manners as seen in FIG. 6 and FIGS. 8 and 9.

As noted above, the diffusion elements of the modes of operation herein are continuously activated and deactivated according to set duty cycles. The total periods for such duty cycles are preferably greater than 0 seconds and less than about 100 seconds, more preferably between about 1/10 second and about 20 seconds, and most preferably between about 1 second and about 10 seconds.

Although specific time periods for activating diffusion elements at particular duty cycles are described herein, such time periods may be altered and/or the number of time periods decreased, so long as the mode of operation seeks to diminish or prevent habituation. Still further, although specific duty cycles are disclosed in the modes of operation herein, such duty cycles may be altered, so long as the mode of operation seeks to diminish or prevent habituation. In particular, additional modes of operation contemplated herein include stepwise increasing of the duty cycle over the same or increasing periods of time.

Diffusion element(s) as referred to herein may be any type of element that promotes diffusion of a volatile material. Examples of diffusion elements include, but are not limited to, aerosol actuators, piezoelectric elements, heaters, fans, nebulizers, and the like. To that effect, any of the modes of operation disclosed herein may be utilized with any type of diffusion element and/or combinations of diffusion elements (e.g. a device that utilizes multiple heaters and a single fan, a device that utilizes a heater to diffuse a first volatile material and a fan to diffuse a second material, etc.).

To that end, although the modes of operation as disclosed herein refer to duty cycles, such modes of operation may be implemented to vary any characteristic of a diffusion element. A characteristic may be any feature of any diffusion element that may be altered to aid in diminishing or preventing habituation. Various characteristics include, but are not limited to speed, intensity, temperature, frequency of actuation, length of actuation, duty cycle, and the like. In one non-limiting embodiment of varying a characteristic, the speed of a fan may be increased according to a mode of operation similar to that of FIGS. 5A and 5B or FIG. 7, so long as such mode of operation aids in diminishing or preventing habituation.

Although the programming as disclosed herein is described as being implemented within the programmable device 202 of the diffuser 30 of FIGS. 1-3, such programming may be implemented in any plug-in type diffuser, including diffusers that emit more than one volatile material. For example, the programming described herein may be implemented in diffusers such as those described in Schroeder et al. U.S. Pat. No. 5,647,053, Schroeder et al. U.S. Pat. No. 5,591,395, Pedrotti et al. U.S. Pat. No. 6,931,202, Pedrotti et al. U.S. Pat. No. 6,862,403, Walter et al. U.S. Pat. No. 6,857,580, Pedrotti et al. U.S. Pat. No. 6,917,754, Martens III, et al. U.S. Pat. No. 4,849,606, Leonard et al. U.S. Pat. No. 5,937,140, Jaworski et al. U.S. Pat. No. 6,478,440, Porchia et al. U.S. application Ser. No. 11/427,714, and Neumann et al. U.S. application Ser. No. 12/319,606, the disclosures of which are incorporated herein in their entirety. Further, such programming may be incorporated into any plug-in type diffusers known in the art that employ a heater.

The volatile materials herein are preferably volatile materials that are susceptible to habituation and/or lose their efficacy after a period of time. Such volatile materials include, but are not limited to, odor eliminators, fragrances, insecticides, insect repellants, insect attractants, disinfectants, air purifiers, aromatherapy scents, antiseptics, deodorizers, air fresheners, and combinations thereof.

INDUSTRIAL APPLICABILITY

The present invention provides methods of dispensing a volatile material from a diffuser, wherein the volatile material is emitted according to pre-established programming that seeks to reduce, minimize, or prevent habituation to the volatile material by the user.

Numerous modifications will be apparent to those skilled in the art in view of the foregoing description. Accordingly, this description is to be construed as illustrative only and is presented for the purpose of enabling those skilled in the art to make and use the present invention and to teach the best mode of carrying out same. All patents and other references cited herein are incorporated by reference in their entirety. The exclusive rights to all modifications which come within the scope of the appended claims are reserved.

I claim:

1. A method of dispensing a volatile material for an operating cycle the method comprising the steps of:

providing power to a volatile material diffuser having a diffusion element;

operating the diffusion element for a first period of time, wherein the diffusion element is continuously activated and deactivated during the period of time at a first duty cycle having a first on time and a first off time;

operating the diffusion element for a final period of time, wherein the diffusion element is continuously activated and deactivated during the final period of time at a final duty cycle having a final on time and a final off time; and ending the operating cycle after the final period of time;

wherein the operating cycle comprises the first period of time and the final period of time, the first duty cycle is less than about 100% such that the first off time is greater than about 0 seconds and the final duty cycle is about 100% such that the final off time is about 0 seconds and wherein the final period of time begins after the first period of time has finished and the final period of time comprises at least about 60% of a total time of the operating cycle.

2. The method of claim 1, wherein the first duty cycle is about 20% and the first period of time is about 5 hours.

3. The method of claim 2, further including the steps of:

operating the diffusion element for a seventh period of time, wherein the diffusion element is continuously activated and deactivated during the period of time at a seventh duty cycle;

operating the diffusion element for a eight period of time, wherein the diffusion element is continuously activated and deactivated during the period of time at a eight duty cycle; and operating the diffusion element for a ninth period of time, wherein the diffusion element is continuously activated and deactivated during the period of time at a ninth duty cycle.

4. The method of claim 3, wherein the first duty cycle is about 10%, the second duty cycle is about 20%, the third duty cycle is about 30%, the fourth duty cycle is about 40%, the fifth duty cycle is about 50%, the sixth duty cycle is about 60%, the seventh duty cycle is about 70%, the eight duty cycle is about 80%, and the ninth duty cycle is about 90%.

5. The method of claim 4, wherein the first period of time is about 24 hours, the second period of time is about 24 hours, the third period of time is about 96 hours, the fourth, fifth, sixth, seventh, eight, and ninth periods of time are about 48 hours, and the final period of time is about 648 hours.

6. The method of claim 1, wherein the first duty cycle is about 10% and the first period of time is about 24 hours.

7. The method of claim 1, further including the steps of:

operating the diffusion element for a second period of time, wherein the diffusion element is continuously activated and deactivated during the period of time at a second duty cycle;

operating the diffusion element for a third period of time, wherein the diffusion element is continuously activated and deactivated during the period of time at a third duty cycle;

operating the diffusion element for a fourth period of time, wherein the diffusion element is continuously activated and deactivated during the period of time at a fourth duty cycle;

operating the diffusion element for a fifth period of time, wherein the diffusion element is continuously activated and deactivated during the period of time at a fifth duty cycle; and operating the diffusion element for a sixth period of time, wherein the diffusion element is continuously activated and deactivated during the period of time at a sixth duty cycle.

8. The method of claim 7, wherein the first duty cycle is about 20%, the second duty cycle is about 33%, the third duty cycle is about 50%, the fourth duty cycle is about 66%, the fifth duty cycle is about 80%, and the sixth duty cycle is about 90%.

9. The method of claim 8, wherein the first time period is about 5 hours, the second time period is about 5 hours, the third time period is about 14 hours, the fourth time period is about 96 hours, the fifth time period is about 120 hours, the sixth time period is about 120 hours, and the final time period is about 720 hours.

10. A method of dispensing a volatile material, the method comprising the steps of:

providing power to a volatile material diffuser having a diffusion element;

operating the diffusion element for a first period of time, wherein the diffusion element is continuously activated and deactivated during the first period of time at a first duty cycle;

interrupting operation of the diffusion element during the first period of time to operate the diffusion element at a second duty cycle for an interrupt period of time; and resuming operation of the diffusion element at the first duty cycle after the interrupt period of time;

wherein the first duty cycle is greater than 0% and less than 100% and the second duty cycle is 100%.

11. The method of claim 10, further including the step of returning to the method of claim 10 after the interrupt period if time and continuing operation from a point at which operation was interrupted.

12. The method of claim 10, wherein the second duty cycle is 100%.

13. The method of claim 10, wherein the interrupt period of time is between about 5 minutes and about 4 hours.

14. The method of claim 13, wherein the step of interrupting occurs after a random period of time.

15. A method of dispensing a volatile material, the method comprising the steps of:

providing power to a volatile material diffuser having a diffusion element;

generating a random number using a random number generator;

multiplying the random number by a time factor to determine a first period of time;

operating the diffusion element for the first period of time, wherein the diffusion element is continuously activated and deactivated during the first period of time at a first duty cycle;

interrupting operation of the diffusion element during the first period of time to operate the diffusion element at a second duty cycle for an interrupt period of time; and resuming operation of the diffusion element at the first duty cycle after the interrupt period of time;

wherein during the first period of time when the first duty cycle is utilized, the diffusion element is alternatingly turned on and off with the on periods being greater than 0% and less than 100% and, during the interrupt period of time when the second duty cycle is utilized, the diffusion element is continuously on.

16. The method of claim 15, wherein the interrupt period of time is between about 5 minutes and about 4 hours.

17. The method of claim 16, wherein the step of interrupting is repeated at least once.

* * * * *